United States Patent
Gao et al.

(10) Patent No.: US 10,416,063 B2
(45) Date of Patent: Sep. 17, 2019

(54) MEASURING ROCK WETTABILITY

(71) Applicant: Saudi Arabian Oil Company, Dhahran OT (SA)

(72) Inventors: Jun Gao, Al Khobar (SA); Ahmad Mubarak Al-Harbi, Dammam (SA); Hyung Tae Kwak, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 162 days.

(21) Appl. No.: 15/801,509

(22) Filed: Nov. 2, 2017

(65) Prior Publication Data

US 2019/0128790 A1    May 2, 2019

(51) Int. Cl.
| | | |
|---|---|---|
| G01V 3/00 | (2006.01) |
| G01N 15/08 | (2006.01) |
| G01R 33/56 | (2006.01) |
| G01N 23/046 | (2018.01) |
| G01R 33/48 | (2006.01) |
| G01N 13/00 | (2006.01) |

(52) U.S. Cl.
CPC ......... *G01N 15/082* (2013.01); *G01N 13/00* (2013.01); *G01N 23/046* (2013.01); *G01R 33/48* (2013.01); *G01R 33/5608* (2013.01); *G01N 2015/0846* (2013.01)

(58) Field of Classification Search
CPC .................................................. G01N 15/082
USPC ...................................... 324/303, 306, 321
See application file for complete search history.

(56) References Cited

U.S. PATENT DOCUMENTS

| | | | |
|---|---|---|---|
| 5,069,065 A | 12/1991 | Sprunt et al. | |
| 6,369,567 B1* | 4/2002 | Song | G01R 33/4625 |
| | | | 324/303 |
| 2012/0241149 A1* | 9/2012 | Chen | G01V 3/32 |
| | | | 166/250.01 |
| 2013/0019659 A1* | 1/2013 | Nadeev | G01N 13/00 |
| | | | 73/38 |
| 2013/0261979 A1* | 10/2013 | Al-Muthana | G01V 3/38 |
| | | | 702/12 |
| 2014/0055134 A1* | 2/2014 | Fordham | G01R 33/4818 |
| | | | 324/309 |

OTHER PUBLICATIONS

Anderson, "Wettability Literature Survey—Part 2: Wettability Measurement," Journal of Petroleum Technology, Nov. 1986, 17 pages.
(Continued)

*Primary Examiner* — Louis M Arana
(74) *Attorney, Agent, or Firm* — Fish & Richardson P.C.

(57) ABSTRACT

A method for characterizing wettability of a porous medium is described. A core sample of the porous medium is secured in a core holder, which includes a first end and a second end. A model of the core sample and a pore volume of the core sample are obtained. A wetting phase is displaced from the core sample by supplying a non-wetting phase at one end of the core holder. The non-wetting phase is displaced from the core sample by supplying the wetting phase at one end of the core holder. A saturation profile of the core sample is determined based on cross-sectional images of the core sample. A wettability index value is calculated at least based on a comparison of the saturation profile and the model of the core sample.

12 Claims, 5 Drawing Sheets

(56) References Cited

OTHER PUBLICATIONS

Brown et al., "Measurements of Fractional Wettability of Oil Fields' Rocks by the Nuclear Magnetic Relaxation Method," 31st Annual Fall Meeting of the Petroleum Branch of the American institute of Mining, Metallurgical, and Petroleum Engineers, Oct. 14-17, 1956, 4 pages.
Craig, "The reservoir engineering aspects of waterflooding," vol. 3, HL Doherty Memorial Fund of AIME, 1971, 142 pages.
Dixit et al., "Empirical Measures of Wettability in Porous Media and the Relationship between Them Derived from Pore-Scale Modelling," Kluwer Academic Publishers, Jul. 2000, 28 pages.
Evans, "Predicting $CO_2$ injectivity properties for application at CCS sites," Curtin University Department of Petroleum Engineering, Jul. 2014, 160 pages.
Hirasaki et al., "Wettability Evaluation During Restored State Core Analysis," Fourth Annual Technical Conference of the Society of Core Analysts, Aug. 15-16, 1990, 28 pages.
Honarpour et al., "Relative permeability of petroleum reservoirs," CRC Press, In., Jan. 1986, 178 pages.
Huang et al., "Capillary End Effects in Coreflood Calculations," 1996 International Symposium of the Society of Core Analysts, Sep. 8-10, 1996, 10 pages.
Huang et al., "Capillary end effects in coreflood calculations," Journal of Petroleum Science and Engineering, Jan. 1998, 15 pages.
Kallel et al., "Modelling the effect of wettability distributions on oil recovery from microporous carbonate reservoirs," Elsevier Ltd., Jun. 2015, 12 pages.
Marrow "Wettability and Its Effect on Oil Recovery," Society of Petroleum Engineers SPE Distinguished Author Series, Dec. 1990, 9 pages.
Neilsen et al., "Determination of Saturation Functions of Tight Core Samples Based on Measured Saturation Profiles," Sep. 1997, 11 pages.
Norgaard et al., "Capillary Pressure Curves for Low Permeability Chalk Obtained by NMR Imaging of Core Saturation Profiles," Society of Petroleum Engineers, Jan. 1995, 10 pages (Presented at the SOE Annual Technical Conference and Exhibition, Oct. 22-25, 1995).
Radke et al., "A Pore-Level Scenario for the Development of Mixed Wettability in Oil Reservoirs," Society of Petroleum Engineers, Jun. 1993, 15 pages. (Presented at the 67th Annual Technical Conference and Exhibition of the Society of Petroleum Engineers, Oct. 4-7, 1992).
Ramakrishnan et al., "A new technique to measure static and dynamic properties of a partially saturated porous medium," Chemical Engineering Science vol. 46, No. 4, Dec. 1991, 7 pages.
Richardson et al., "Laboratory Determination of Relative Permeability," Journal of Petroleum Technology, Aug. 1952, 11 pages.
Romanenko et al., "An assessment of non-wetting phase relative permeability in water-wet sandstones based on quantitative MRI of capillary end effects," Journal of Petroleum Science and Engineering, Elsevier Ltd., Sep. 2013, 7 pages.
Salathiel et al., "Oil Recovery by Surface Film Drainage in Mixed-Wettability Rocks," Journal of Petroleum Technology, Oct. 1973, 9 pages.
International Search Report and Written Opinion issued in International Application No. PCT/US2018/056984 dated Feb. 12, 2019, 14 pages.
Al-Mahrooqi et al., "Pore-scale modelling of NMR relaxation for the characterization of wettability," Journal of Petroleum Science and Engineering, Elsevier, vol. 52, No. 1-4, Jun. 2006, 15 pages.

* cited by examiner

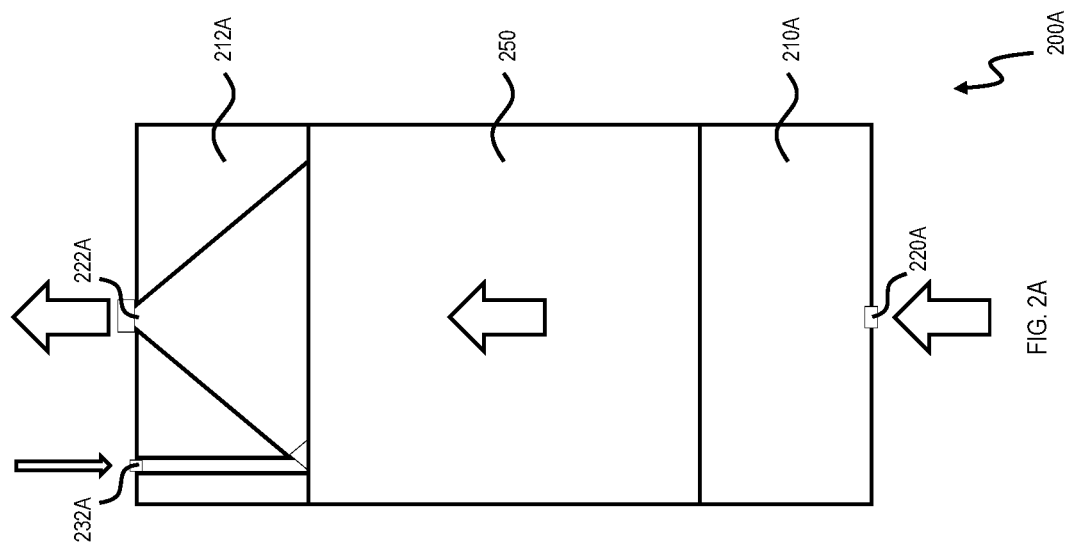

MEASURING ROCK WETTABILITY

TECHNICAL FIELD

This specification relates to characterizing wettability of rock formations.

BACKGROUND

Wettability is the tendency of a fluid to spread across or adhere to a solid surface in the presence of other immiscible fluids. Wettability can describe the preference of a solid to be in contact with one fluid rather than another. In relation to the oil and gas industry, wettability can refer to the interaction between fluids such as hydrocarbons or water and a reservoir rock. The wettability of a reservoir can affect the hydrocarbon extraction process. Porous media, such as carbonate rock, can be complex and can have several configurations in different areas of the same formation due to the varied geometry and mineralogy of its pore space. The wettability of such rock formations can therefore be heterogeneous. A shift in wettability toward water-wetness can allow the extraction of additional hydrocarbons from a rock formation. Heterogeneous wettability and induced wettability alterations have gained increased attention in order to improve enhanced hydrocarbon recovery techniques.

SUMMARY

The present disclosure describes technologies relating to characterizing wettability of rock formations, taking into consideration capillary end effect. Certain aspects of the subject matter described here can be implemented as a method for characterizing wettability of a porous medium. A core sample of the porous medium is secured in a core holder, which includes a first end and a second end. The first end and the second end are used to allow fluid to enter or exit the core holder. A model of the core sample and a pore volume of the core sample are obtained. A wetting phase is displaced from the core sample by supplying a non-wetting phase at one of the first end of the core holder or the second end of the core holder while supplying the wetting phase to a first different one of the first end of the core holder or the second end of the core holder. The non-wetting phase is displaced from the core sample by supplying the wetting phase at one of the first end of the core holder or the second end of the core holder while supplying the non-wetting phase to a second different one of the first end of the core holder or the second end of the core holder. A saturation profile of the core sample is determined based on cross-sectional images of the core sample. A wettability index value is calculated at least based on a comparison of the saturation profile and the model of the core sample.

This, and other aspects, can include one or more of the following features. The core holder has a vertical axis and a vertical orientation, and the first end and the second end are parallel to the vertical axis of the core holder. At least one of the first end or the second end can be conical and can be used to maintain contact between the wetting phase or the non-wetting phase and the core sample.

Obtaining the model and the pore volume can include scanning the core sample in a dry state.

Displacing the wetting phase from the core sample can include injecting the non-wetting phase at a rate of substantially 4 cubic centimeters per hour ($cm^3/hr$) for at least 10 pore volumes, and displacing the non-wetting phase from the core sample can include injecting the wetting phase at a rate of substantially 4 $cm^3/hr$ for at least 10 pore volumes.

The core sample can be prepared for core flooding. Preparing the core sample for core flooding can include saturating the core sample with the wetting phase, displacing the wetting phase from the core sample with the non-wetting phase until steady state is reached, and aging the core sample.

The porous medium can include a reservoir rock, and the core sample can be aged for at least 4 weeks.

Determining the saturation profile of the core sample based on cross-sectional images of the core sample can be repeated after saturating the core sample with the wetting phase, while displacing the wetting phase from the core sample, and while displacing the non-wetting phase from the core sample.

The non-wetting phase can include a hydrocarbon fluid, and the wetting phase can include a brine solution.

Determining the saturation profile of the core sample can include scanning the core sample using magnetic resonance imaging (MRI), and the brine solution can be a deuterium oxide-based brine solution.

Scanning the core sample using MRI can include scanning the core sample to obtain multiple images and producing an average across the multiple images to increase a signal-to-noise ratio (SNR).

Determining the saturation profile of the core sample can include scanning the core sample using X-ray computed tomography (CT).

The wetting phase can include an attenuating agent, which can be used to decrease detection of the wetting phase by X-ray CT scanning.

The subject matter described in this specification can be implemented in particular implementations, so as to realize one or more of the following advantages. The measurement and characterization of wettability can take relatively shorter time to complete in comparison to similar displacement techniques. The measurement of wettability takes advantage of non-intrusive scanning techniques, so that additional tests can be conducted on the same core sample. The wettability index, which takes into consideration the capillary end effect, can be used to improve subsequent testing (such as providing insight to define experiment parameters like injection flow rate) and can also be used in conjunction with information obtained from any additional tests on the same core sample to provide a more comprehensive understanding of the core sample, which can shed insight for improving hydrocarbon extraction from a reservoir.

The details of one or more implementations of the subject matter of this specification are set forth in the accompanying drawings and the description. Other features, aspects, and advantages of the subject matter will become apparent from the description, the drawings, and the claims.

DESCRIPTION OF DRAWINGS

FIG. 2A is a diagram of an example of a core holder.

DETAILED DESCRIPTION

Figure 1:
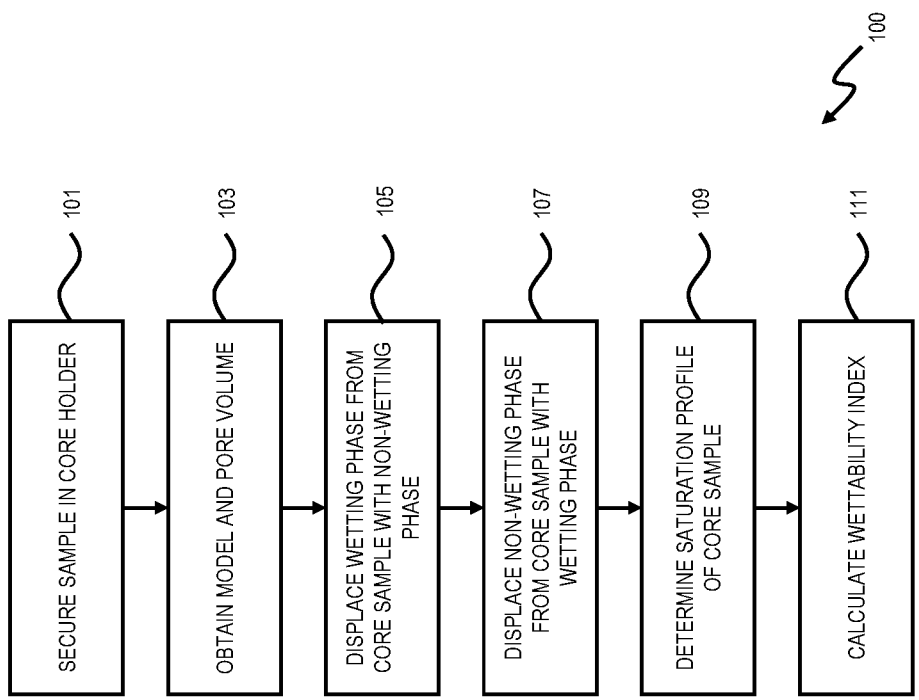
FIG. 1 is a flow chart of an example of a method for determining wettability of a rock sample.

A drop of a preferentially wetting fluid (the wetting phase) can displace another fluid (the non-wetting phase). In extreme cases, the wetting phase can spread over an entire surface. On the other hand, if a non-wetting fluid is dropped onto a surface already covered by the wetting fluid, the non-wetting fluid can bead up, which reduces its contact with the solid. Intermediate-wet (sometimes referred to as neutrally wet) describes a surface that does not show a preference to either fluid—for example, a rock surface is intermediate-wet if the surface is equally oil- and water-wet. Another type of wettability is heterogeneous wettability (sometimes referred to as fractional wettability), which can be seen in cases where portion of a rock are strongly oil-wet, whereas other portions of the same rock are strongly water wet. Heterogeneous wettability can occur due to variation in minerals with different surface chemical properties. Another type of wettability is mixed wettability, which can be seen in cases where small pores are occupied by water and are water-wet, while larger pores are continuous and oil-wet.

Various methods can quantify oil or water wettability of a rock surface. One possible measure of wettability of a solid surface is defined by a contact angle of a fluid with the surface in the presence of another immiscible fluid—for example, a hydrocarbon oil droplet on a rock surface in the presence of water or brine. A rock surface can be described as being water-wet, intermediate-wet, or oil-wet, which translate to contact angle ranges of 0° to 75°, 75° to 105°, and 105° to 180°, respectively. The terms "water-wet", "intermediate-wet", and "oil-wet" are qualitative characterizations of a rock surface, and the contact angle ranges for each kind of wetness may deviate from the previous ranges. Other methods, such as displacement methods, quantify wettability in the form of an index value, which categorizes a surface as being water-wet, oil-wet, or intermediate-wet. The United States Bureau of Mines (USBM) method and the Amott method are a couple of examples of displacement methods that can be used to characterize wettability. Core flooding and centrifuging are examples of displacement techniques for displacing a wetting or non-wetting phase from a surface. Displacement experiments involve two basic steps of displacement: imbibition and drainage. Imbibition occurs when a wetting fluid displaces a non-wetting fluid. Drainage occurs when a non-wetting fluid displaces a wetting fluid. In displacement experiments, due to capillary discontinuity, the wetting phase tends to remain at the core outlet during core flooding displacements. This tendency is referred to as the capillary end effect (CEE). Capillary end effect can exist in any multi-phase core flooding displacements, and the capillary end effect, in some cases, can cause significant errors in calculation of saturation and permeability of a core sample. At steady flow during core flooding experiments, the saturation may not be uniform due to the capillary end effect.

The following detailed description describes technologies relating to characterizing wettability of rock formations, taking into consideration the capillary end effect, and is presented to enable any person skilled in the art to make and use the disclosed subject matter in the context of one or more particular implementations. Various modifications, alterations, and permutations of the disclosed implementations can be made and will be readily apparent to those of ordinary skill in the art, and the general principles defined may be applied to other implementations and applications, without departing from scope of the disclosure. In some instances, details unnecessary to obtain an understanding of the described subject matter may be omitted so as to not obscure one or more described implementations with unnecessary detail and to the extent that such details are within the skill of one of ordinary skill in the art. The present disclosure is not intended to be limited to the described or illustrated implementations, but to be accorded the widest scope consistent with the described principles and features.

Figure 2B:
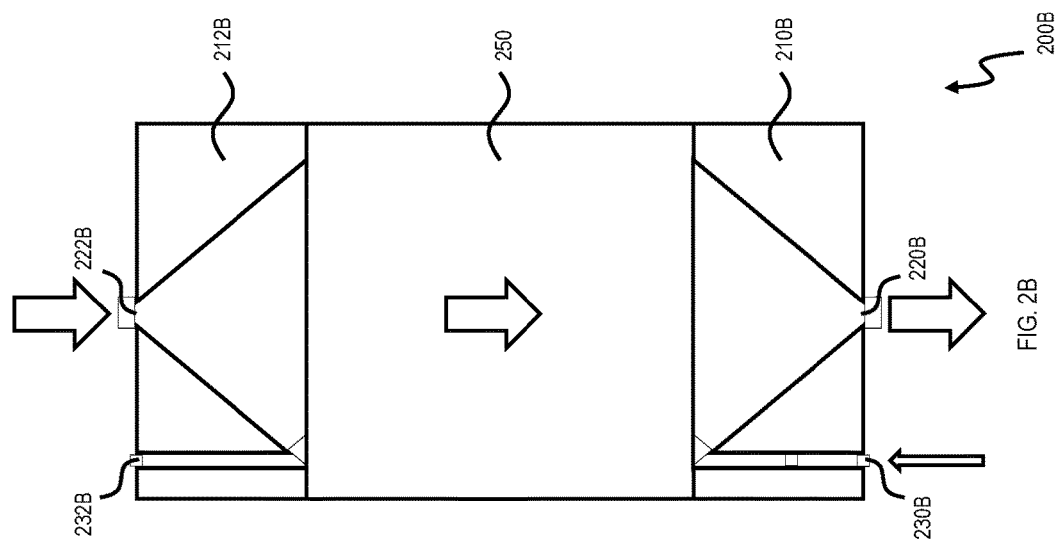
FIG. 2B is a diagram of an example of a core holder.

FIG. 1 is a flow chart of a method 100 for characterizing wettability of a porous medium, such as carbonate rock. At 101, a core sample of the porous medium is secured in a core holder. Examples of the core holder are shown in FIGS. 2A and 2B. Referring to the core holder 200A shown in FIG. 2A, the core holder 200A includes a first end 210A and a second end 212A, and the ends (210A, 212A) can allow fluid to enter or exit the core holder 200A. The core holder can have a vertical axis and a vertical orientation, and the ends (210A, 212A) can be parallel to the vertical axis. For the purposes of consistency and clarity, the bottom end of the core holder is referred to as the first end (210A or 210B for FIG. 2B), and the top end of the core holder is referred to as the second end (212A or 212B for FIG. 2B) in this disclosure.

Referring back to FIG. 1, at 103, a pore volume and a model of the core sample are obtained. In certain implementations, the pore volume and the model of the core sample are obtained by scanning the core sample in a dry state. The scanning of the core sample can be conducted, for example, using magnetic resonance imaging (MRI) or X-ray computed tomography (CT). Depending on the sensitivity of the equipment, image scanning can capture background noise that interferes with the desired signal. In the case that MRI is used, the core sample can be scanned multiple times to obtain multiple images, and then an average across the multiple images can be produced to improve (that is, increase) the signal-to-noise ratio (SNR). Additionally, the core sample can undergo various preparation steps before moving onto 105. For example, the core sample can be fully saturated with a wetting phase, such as a brine solution. Then a saturation profile of the saturated core sample can be determined based on cross-sectional images of the core sample (by using, for example, MRI or X-ray CT scanning). In some cases, the brine solution is removed from the core sample with a Dean-Stark apparatus using a solvent such as acetone or methanol, and then the core sample is re-saturated with a deuterium oxide-based brine solution. In certain implementations, the saturation profile of the saturated core sample can be compared to the model of the core sample, which is obtained by scanning the core sample in a dry state. In the case that MRI is used, and the synthesized brine is based on deuterium oxide, the saturation profile of the saturated core sample and the model of the core sample in a dry state can be substantially the same because deuterium oxide is invisible to MRI. In this specification, "substantially" means a deviation or allowance of up to 10 percent (%) and any variation from a mentioned value is within the tolerance limits of any machinery used to manufacture the part.

The wetting phase can be displaced from the core sample with a non-wetting phase, such as hydrocarbon fluid (for example, oil). The displacement can be achieved, for example, by injecting oil into the core sample through the first or second end of the core holder. Oil can be continually injected until steady state is reached—that is, substantially no additional wetting phase fluid (brine) is displaced from the core sample. The core sample can then be aged for a period of time. In the case that the porous medium to be studied is a reservoir rock (that is, the core sample is a sample of reservoir rock), then the core sample is aged for at least 4 weeks. In certain implementations, the core sample is aged under reservoir conditions. In cases where the reservoir temperature and pressure are known and below maximum (or design) pressure and temperature of the utilized equipment, the reservoir temperature and pressure can be used. In cases where the reservoir temperature and pressure are known and above maximum (or design) pressure and temperature of the utilized equipment, the maximum (or design) pressure and temperature of the utilized equipment can be used. In cases where the reservoir temperature and pressure are unknown, a temperature of substantially 80° C. and a pressure of substantially 2,000 psig, for example, can be used. As one example, the core sample can be aged under a confining pressure of 2,000 pounds per square inch gauge (psig).

At 105, a wetting phase is displaced from the core sample by supplying a non-wetting phase at either the first or second end of the core holder, while supplying the wetting phase to the other end of the core holder. As one example, the non-wetting phase can be supplied at the first end, while the wetting phase is supplied at the second end at a lower rate than the non-wetting phase. For example, the non-wetting phase can be injected at a rate of substantially 4 cubic centimeters per hour ($cm^3/hr$) for at least 10 pore volumes, while the wetting phase is injected at a rate of substantially 1 $cm^3/hr$ or less. In this case, because the rate of fluid provided at the first end is higher than the rate of fluid provided at the second end, the first end can be considered the inlet end of the core sample, and the second end can be considered the outlet end of the core sample. Step 105 can be referred to as the oil flooding step or a forced drainage step. The second end can be conical and can be used to maintain contact between the wetting phase and the outlet end of the core sample. In certain implementations, the wetting phase is a deuterium oxide-based brine, and the non-wetting phase is a hydrocarbon oil. Because brine is heavier than oil (that is, brine has a higher density than oil), the brine tends to fall in comparison to the oil due to gravity, resulting in a stable capillary end effect observed at the outlet end (top end) of the core sample during 105.

At 107, the non-wetting phase is displaced from the core sample by supplying the wetting phase at either the first or second end of the core holder, while supplying the non-wetting phase to the other end of the core holder. In certain implementations, steps 105 and 107 can be the same, except that the rate at which the wetting and non-wetting phases are injected are switched. As one example, the wetting phase can be supplied at the second end, while the non-wetting phase is supplied at the first end at a lower rate than the wetting phase. For example, the wetting phase can be injected at a rate of substantially 4 $cm^3/hr$ for at least 10 pore volumes, while the non-wetting phase is injected at a rate of substantially 1 $cm^3/hr$ or less. In this case, because the rate of fluid provided at the second end is higher than the rate of fluid provided at the first end, the second end can be considered the inlet end of the core sample, and the first end can be considered the outlet end of the core sample. Step 107 can be referred to as the water flooding (or brine flooding) step or a forced imbibition step. The first end can be conical and can be used to maintain contact between the non-wetting phase and the outlet end of the core sample. Because oil is lighter than brine (that is, oil has a lower density than brine), the oil tends to rise in comparison to the brine due to gravity, resulting in a stable capillary end effect observed at the outlet end (bottom end) of the core sample during 107. The descriptions of steps 105 and 107 exploit the density differences of the wetting and non-wetting fluids. The wetting and non-wetting phases can optionally be injected at different ends from those that are described previously (in other words, the first end and second ends can be switched), depending on various factors, such as the core sample used, the wetting phase used, the non-wetting phase used, and the type of scanning used to obtain images (and subsequent saturation profiles) of the core sample. Steps 105 and 107 can be performed at an elevated pressure. For example, a back pressure (that is, the pressure at the outlet end) can be maintained by a back pressure regulator to be set at the reservoir pressure (or 2,000 psig if the reservoir pressure is unknown). The inlet pressure would then be the sum of differential pressure across the core holder (that is, the differential pressure of fluid flowing through the core sample in the core holder) and the back pressure.

Figure 3A:
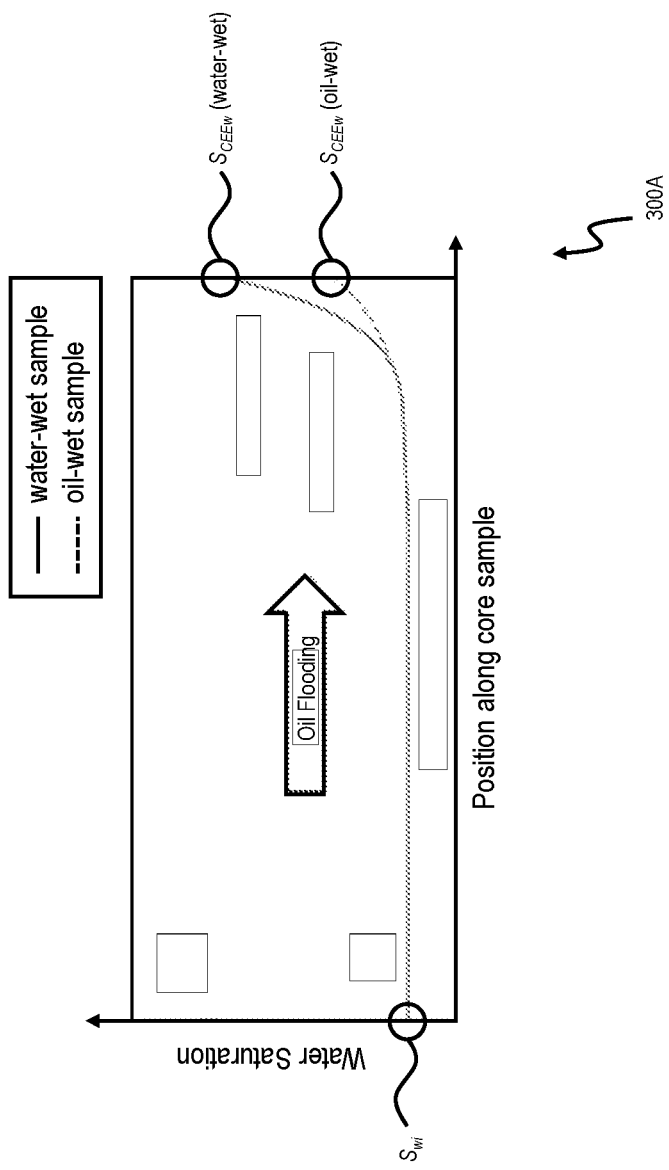
FIGS. 3A & 3B are graphs of an example of a saturation profile.
Figure 3B:
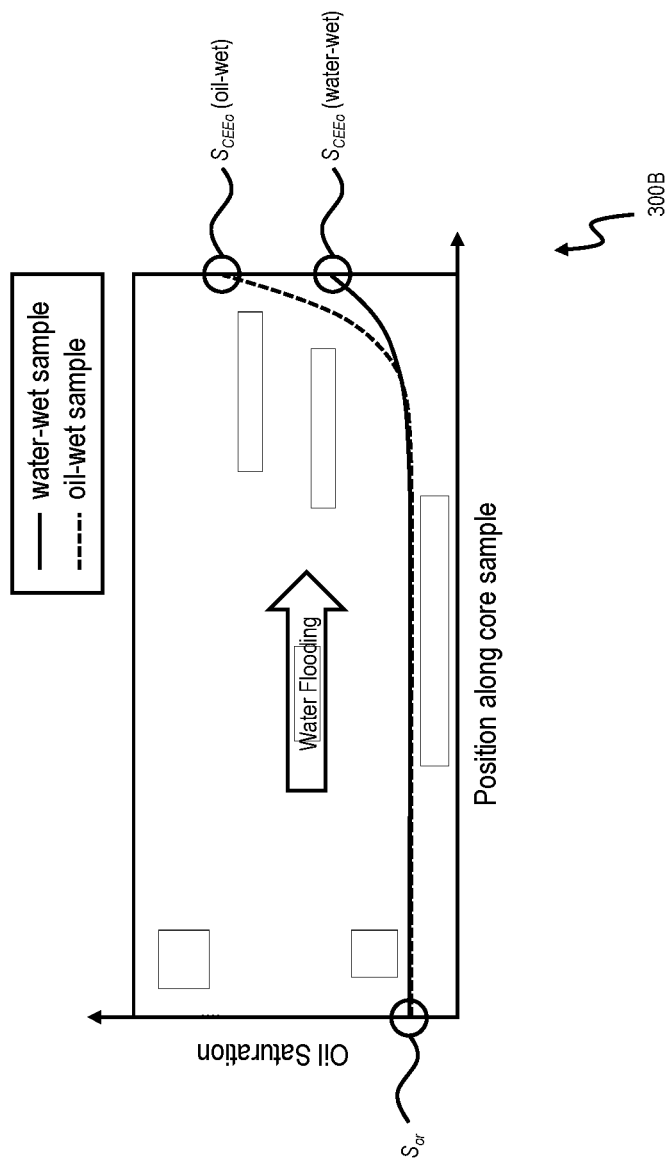

At 109, a saturation profile of the core sample is determined based on cross-sectional images of the core sample. The saturation profile of the core sample can be determined based on cross-sectional images of the core sample (by using, for example, MRI or X-ray CT scanning). An example of a saturation profile is shown in FIGS. 3A-3B. Determining the saturation profile of the core sample based on images of the core sample can be repeated after or during multiple steps of method 100. In certain implementations, determining the saturation of the core sample based on cross-sectional images of the core sample is repeated after saturating the core sample with the wetting phase (during core sample preparation), while displacing the wetting phase from the core sample at 105, and while displacing the non-wetting phase from the core sample at 107. The saturation profiles can be determined based on a comparison of the image obtained during or after a step with the model of the core sample obtained at 103 or the fully saturated core sample obtained during the core sample preparation. The saturation can be determined based on the wetting phase (for example, water saturation) or the non-wetting phase (for example, oil saturation). In the cases that X-ray CT scanning is used to obtain images of the core sample, the wetting phase (that is, the brine solution), can include attenuating agents, which can decrease detection of the wetting phase by X-ray CT scanning. For example, the wetting phase can be an aqueous solution of 5% sodium iodide (NaI). An attenuating agent can increase the contrast or distinction between the wetting phase (brine solution) and the non-wetting phase (oil). In some cases, the density difference between the wetting phase and the non-wetting phase is large enough that attenuating agents may not be necessary.

At 111, a wettability index value is calculated based on a comparison of the saturation profile and the model of the core sample. The saturation at each end of the core sample from the saturation profiles obtained at 109 can be used to calculate wettability index values. Because the capillary end effect is considered, the wettability index values can be referred to as CEE wettability index values. Four saturation values (irreducible water saturation, CEE water saturation, CEE oil saturation, residual oil saturation) can be used to calculate three CEE wettability index values (CEE water-wetness index $I_{CEEw}$, CEE oil-wetness index $I_{CEEo}$, CEE wettability index $I_{CEE}$). Saturation can be expressed as a fraction, percent, or decimal and is equal to the ratio of a given fluid in the total pore volume of the core sample. For example, if water occupies 32% of the pore volume of the core sample, then the core sample has a water saturation of 32% (which can also be expressed as 0.32 or $32/100$). In the case that oil and water are present in the pore volume of the core sample, then the 32% water saturation can translate to a 68% oil saturation (which can also be expressed as 0.68 or $68/100$). Assuming the wetting phase is a brine solution, and the non-wetting phase is a hydrocarbon fluid, the saturation values can be obtained by the following comparisons. The residual oil saturation ($S_{or}$) and the CEE oil saturation ($S_{CEEo}$) can be determined based on a comparison of the saturation profile obtained at 105 (water flooding) and the saturation profile obtained during core sample preparation (core sample saturated with brine). The irreducible water saturation ($S_{wi}$) and CEE water saturation ($S_{CEEw}$) can be determined based on a comparison of the saturation profile obtained at 107 (oil flooding) and the saturation profile obtained during core sample preparation (core sample saturated with brine).

The CEE index values can be calculated using the following equations:

$$I_{CEEw} = \frac{S_{CEEw} - S_{wi}}{1 - S_{wi} - S_{or}} \quad (1)$$

$$I_{CEEo} = \frac{S_{CEEo} - S_{or}}{1 - S_{wi} - S_{or}} \quad (2)$$

$$I_{CEE} = I_{CEEw} - I_{CEEo} \quad (3)$$

CEE water-wetness index ($I_{CEEw}$) values and CEE oil-wetness index ($I_{CEEo}$) values can be in a range of 0 to 1. CEE wettability index ($I_{CEE}$) values can be in a range of −1 (oil-wet) to 1 (water-wet).

FIG. 2A is a diagram of an example core holder 200A that can be used to secure a core sample 250 during core flooding experiments to measure and characterize wettability. The illustrated core holder 200A has vertical orientation and includes a first end 210A and a second end 212A. In certain implementations, the first end 210A can be below the second end 212A. In other words, the first end 210A can be the bottom end of the core holder 200A, and the second end 212A can be the top end of the core holder 200A. In some cases, the first end 210A and the second end 212A are switched. The first end 210A and the second end 212A are configured to allow fluid to enter or exit the core holder 200A and are parallel to the vertical axis of the core holder 200A. A core sample 250 can be secured in the core holder 200A between the first end 210A and the second end 212A. The core sample 250 can also have a vertical orientation while secured in the core holder 200A. The first end, the second end, or both ends can be conical. The descriptors "first" and "second" are simply nominal characterizations of the ends of the core holder 200A and are used for consistency throughout the disclosure. In certain implementations, the first end 210A can include port 220A to allow fluid to enter or exit the core holder 200A at the first end 210A. In certain implementations, the second end 212A can include ports 222A and 232A to allow fluid to enter or exit the core holder 200A at the second end 212A.

In certain implementations, the second end 212A is conical and is configured to inject fluid at the second end 212A (for example, by injecting fluid through port 232A), such that contact can be maintained between the fluid injected at the second end 212A and the core sample 250. As one example, a non-wetting phase can be injected at the first end 210A (for example, by injecting the non-wetting phase through port 220A), so that the non-wetting phase can displace a wetting phase from the core sample 250. The wetting phase can be injected at the second end 212A (for example, by injecting the wetting phase through port 232A) at a lower rate in comparison to the non-wetting phase, so that the average, overall flow of fluid through the core holder 200A is upward. Assuming that the wetting phase is deuterium oxide-based brine and the non-wetting phase is oil, the wetting phase tends to fall in comparison to the non-wetting phase due to the difference in density. Injection of the wetting phase at the second end 212A can allow for the wetting phase to maintain contact with the outlet end of the core sample 250. Therefore, the capillary end effect can be established during the displacement step 105 (oil flooding) of method 100 (referring back to FIG. 1). By switching the wetting phase and non-wetting phase injections (that is, wetting phase injected at the first end 210A through port 220A, and non-wetting phase injected at the second end 212A through port 232A at a lower rate than the wetting phase), a stable capillary end effect can be established during the displacement step 107 (water flooding) of method 100.

FIG. 2B is a diagram of an example core holder 200B that can be used to secure a core sample 250 during core flooding experiments to measure and characterize wettability. The illustrated core holder 200B (shown in FIG. 2B) is substantially the same as the core holder 200A (shown in FIG. 2A), but the first end 210B is also conical and can allow a fluid to be injected at the first end 210B, such that contact can be maintained between the fluid injected at the first end 210B and the core sample 250. In certain implementations, the first end 210B can include ports 220B and 230B to allow fluid to enter or exit the core holder 200B at the first end 210B. In certain implementations, the second end 212B can include ports 222B and 232B to allow fluid to enter or exit the core holder 200B at the second end 212B. As one example, a wetting phase can be injected at the second end 212B (for example, by injecting the wetting phase through port 222B), so that the wetting phase can displace a non-wetting phase from the core sample 250. The non-wetting phase can be injected at the first end 210B (for example, by injecting the non-wetting phase through port 230B) at a lower rate in comparison to the non-wetting phase, so that the average, overall flow of fluid through the core holder 200B is downward. Assuming that the wetting phase is deuterium oxide-based brine and the non-wetting phase is oil, the non-wetting phase tends to rise in comparison to the wetting phase due to the difference in density. Injection of the non-wetting phase at the first end 210B can allow for the non-wetting phase to maintain contact with the outlet end of the core sample 250. Therefore, a stable capillary end effect can be established during the displacement step 107 (water flooding) of method 100 (referring back to FIG. 1). By switching the injection rates of the wetting phase and non-wetting phase injections—that is, injecting the non-wetting phase through port 220B at a higher rate in comparison to injecting the wetting phase through port 232B, so that the average, overall flow of fluid through the core holder 200B is upward—a stable capillary end effect can be established during the displacement step 105 (oil flooding) of method 100.

FIGS. 3A-3B are graphs of an example water saturation profile 300A of a core sample during oil flooding (step 105 of method 100). Once the oil flooding has reached steady state (that is, substantially no additional water is being displaced from the core sample, which, for example, can be after oil injection of at least 10 pore volumes), the core sample can be scanned to obtain images of the core sample. A comparison of the images with the model of the dry core sample or the saturation profile of the fully saturated core sample can be used to determine the saturation profile 300A of the core sample. The water saturation at the inlet end of the core sample provides the irreducible water saturation ($S_{wi}$), and the water saturation at the outlet end of the core sample provides the CEE water saturation ($S_{CEEw}$). For more water-wet core samples, the CEE water saturation can increase. For example, in FIG. 3A, the solid curve can represent a saturation profile of a core sample that is more water-wet than a core sample whose saturation profile is represented by the dotted curve.

FIG. 3B is a graph of an example oil saturation profile 300B of a core sample during water flooding (step 107 of method 100). Once the water flooding has reached steady state (that is, substantially no additional oil is being displaced from the core sample, which, for example, can be after water injection of at least 10 pore volumes), the core sample can be scanned to obtain images of the core sample. A comparison of the images with the model of the dry core sample or the saturation profile of the fully saturated core sample can be used to determine the saturation profile 300B of the core sample. The oil saturation at the inlet end of the core sample provides the residual oil water saturation ($S_{or}$), and the oil saturation at the outlet end of the core sample provides the CEE oil saturation ($S_{CEEo}$). For more oil-wet core samples, the CEE oil saturation can increase. For example, in FIG. 3B, the solid curve can represent a saturation profile of a core sample that is more oil-wet than a core sample whose saturation profile is represented by the dotted curve.

If water (or brine) and oil occupy the pore volume of the core sample, then water saturation and oil saturation of the core sample balance to 1. In relation to each other, the CEE water saturation is lower than the water saturation at residual oil condition, and the CEE oil saturation is lower than the oil saturation at irreducible water condition.

$$S_{CEEw} < 1 - S_{or} \quad (4)$$

$$S_{CEEo} < 1 - S_{wi} \quad (5)$$

As seen in FIGS. 3A and 3B, two saturation values ($S_{wi}$, $S_{CEEw}$) can be obtained at the forced drainage step (oil flooding 105 of method 100), and two saturation values ($S_{or}$, $S_{CEEo}$) can be obtained at the forced imbibition step (water flooding 107 of method 100). The Amott method includes spontaneous imbibition and spontaneous drainage steps, which can each take several days, to obtain spontaneous oil saturation and spontaneous water saturation values, respectively, in order to calculate the Amott or Amott-Harvey index values. The method 100 obtains the saturation values ($S_{wi}$, $S_{CEEw}$, $S_{CEEo}$, $S_{or}$) without requiring the waiting associated with spontaneous imbibition and spontaneous drainage steps in order to calculate the CEE wettability index values ($I_{CEEw}$, $I_{CEEo}$, $I_{CEE}$) and characterize the wettability of the core sample, thereby saving time.

While this specification contains many specific implementation details, these should not be construed as limitations on the scope of any invention or on the scope of what may be claimed, but rather as descriptions of features that may be specific to particular implementations of particular inventions. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results.

Accordingly, the previously described example implementations do not define or constrain this disclosure. Other changes, substitutions, and alterations are also possible without departing from the spirit and scope of this disclosure.

What is claimed is:

1. A method for characterizing wettability of a porous medium, the method comprising:

securing a core sample of the porous medium in a core holder, the core holder comprising a first end and a second end, the first end and the second end configured to allow fluid to enter or exit the core holder;

obtaining a model of the core sample and a pore volume of the core sample;

displacing a wetting phase from the core sample by supplying a non-wetting phase at one of the first end of the core holder or the second end of the core holder while supplying the wetting phase to a first different one of the first end of the core holder or the second end of the core holder;

displacing the non-wetting phase from the core sample by supplying the wetting phase at one of the first end of the core holder or the second end of the core holder while supplying the non-wetting phase to a second different one of the first end of the core holder or the second end of the core holder;

determining a saturation profile of the core sample based on cross-sectional images of the core sample; and calculating a wettability index value at least based on a comparison of the saturation profile and the model of the core sample.

2. The method of claim 1, wherein the core holder has a vertical axis and a vertical orientation, wherein the first end and the second end are parallel to the vertical axis of the core holder, and at least one of the first end or the second end is conical and configured to maintain contact between the wetting phase or the non-wetting phase and the core sample.

3. The method of claim 1, wherein obtaining the model and the pore volume comprises scanning the core sample in a dry state.

4. The method of claim 3, wherein displacing the wetting phase from the core sample comprises injecting the non-wetting phase at a rate of substantially 4 cubic centimeters per hour (cm³/hr) for at least 10 pore volumes, and displacing the non-wetting phase from the core sample comprises injecting the wetting phase at a rate of substantially 4 cm³/hr for at least 10 pore volumes.

5. The method of claim 3, further comprising preparing the core sample for core flooding, the preparing the core sample for core flooding comprising:

saturating the core sample with the wetting phase;

displacing the wetting phase from the core sample with the non-wetting phase until steady state is reached; and aging the core sample.

6. The method of claim 5, wherein the porous medium comprises a reservoir rock, and the core sample is aged for at least 4 weeks.

7. The method of claim 6, wherein determining the saturation profile of the core sample based on cross-sectional images of the core sample is repeated:
- after saturating the core sample with the wetting phase;
- while displacing the wetting phase from the core sample; and
- while displacing the non-wetting phase from the core sample.

8. The method of claim 7, wherein the non-wetting phase comprises a hydrocarbon fluid, and the wetting phase comprises a brine solution.

9. The method of claim 8, wherein determining the saturation profile of the core sample comprises scanning the core sample using magnetic resonance imaging (MRI), and the brine solution is a deuterium oxide-based brine solution.

10. The method of claim 9, wherein scanning the core sample using MRI comprises scanning the core sample to obtain a plurality of images and producing an average across the plurality of images to increase a signal-to-noise ratio (SNR).

11. The method of claim 8, wherein determining the saturation profile of the core sample comprises scanning the core sample using X-ray computed tomography (CT).

12. The method of claim 11, wherein the wetting phase comprises an attenuating agent configured to decrease detection of the wetting phase by X-ray CT scanning.

\* \* \* \* \*